United States Patent [19]

Susi

[11] 4,125,518

[45] Nov. 14, 1978

[54] 1-OXA-4-AZASPIRO[4,5]DECANES AS LIGHT STABILIZERS FOR POLYMERS

[75] Inventor: Peter V. Susi, Middlesex, N.J.

[73] Assignee: American Cyanamid Company, Stamford, Conn.

[21] Appl. No.: 891,570

[22] Filed: Mar. 30, 1978

[51] Int. Cl.$^2$ ............................................... C08K 5/35
[52] U.S. Cl. ............................. 260/45.8 NZ; 106/176; 260/45.7 PH; 260/45.75 N; 260/45.85 B; 260/307 FA
[58] Field of Search ................................ 260/45.8 NZ

[56] References Cited

U.S. PATENT DOCUMENTS

| 2,817,663 | 12/1957 | Conlon et al. | 260/45.8 NZ |
|---|---|---|---|
| 2,995,540 | 8/1961 | Duennenberger et al. | 260/45.8 NZ |
| 3,380,959 | 4/1968 | Frump | 260/45.8 NZ |
| 3,542,729 | 11/1970 | Murayama et al. | 260/45.8 NZ |
| 3,836,505 | 9/1974 | Buell | 260/45.8 NZ |
| 3,864,354 | 2/1975 | Irick, Jr. et al. | 260/45.8 NZ |

Primary Examiner—Melvyn I. Marquis
Assistant Examiner—R. A. White
Attorney, Agent, or Firm—Bruce F. Jacobs

[57] ABSTRACT

This invention relates to the use of 1-oxa-4-azaspiro[4,5]decanes as light stabilizers for polymers.

8 Claims, No Drawings

1-OXA-4-AZASPIRO[4,5]DECANES AS LIGHT STABILIZERS FOR POLYMERS

This invention relates to light stable polymer compositions. More particularly, this invention relates to the use of compounds represented by formula (I)

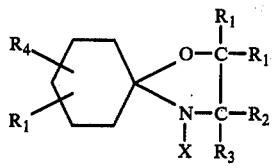
(I)

wherein each $R_1$ is selected from hydrogen and alkyl having about 1 to 8 carbon atoms, $R_2$ and $R_3$ are each selected from alkyl or hydroxyalkyl having about 1 to 8 carbon atoms, $R_4$ is hydrogen or alkyl having 1 to 18 carbon atoms, and X is H, —OH, —O·, or alkyl having 1 to 8 carbon atoms, to stabilize polymers, particularly polyolefins, against degradation by ultraviolet radiation.

It is well-known that sunlight and other sources of ultraviolet radiation cause degradation of polymers as evidenced by embrittlement or yellowing of plastic articles made therefrom. It is also well-known that this degradation can be inhibited by incorporating light stabilizer additives in or on such articles. Continuing efforts are being made to discover ultraviolet light stabilizers which will be superior to those currently available.

German Pat. No. 2,126,797 of Sankyo Co. Ltd., discloses the use of:

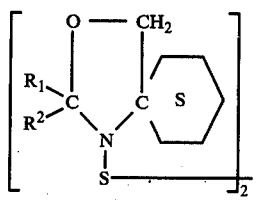

as a heat and light stabilizer for polymers. The present invention, to the contrary, avoids the disulfide linkage and has the spiro cyclohexyl radical immediately between the oxygen and nitrogen atoms.

In accordance with the present invention there is provided a polymer composition containing an amount of a compound of formula (I) effective to stabilize the polymer against degradation by ultraviolet radiation.

Preferably, the polymer is a polyolefin. More preferably, the polyolefin is polypropylene.

In accordance with the present invention there is also provided a method for stabilizing a polymer against degradation by ultraviolet radiation by incorporating therein an effective amount of a compound of formula (I).

Polymers which are stabilized against degradation by ultraviolet light using the compounds of the present invention include polyvinyl chloride, polyvinylidene chloride, copolymers of vinyl chloride and vinylidene chloride, polystyrene, polyesters, cellulose acetate, polyvinyl acetate, polyvinyl fluoride, polymethyl methacrylate, polyurethanes, polycarbonates and natural and synthetic rubbers such as polymers of acrylonitrile, butadiene, and styrene. They are particularly useful in polyolefins, such as polyethylene and polypropylene. These compounds may be incorporated in or on such polymers by any of the various standard procedures known in the art for such purpose, such as by dry blending the additive with the polymer in powder or granular form followed by molding or extruding, by milling, by immersing the polymer as film, sheet, fibers, etc. in a solution of the additive in an appropriate solvent (as in a dye process), etc.

The polymer composition should contain an effective stabilizing amount of the compound of formula (I), which amount will depend on the nature of the polymer and the amount of exposure to ultraviolet light to which the composition will be subjected. Generally, an amount between about 0.1% and 5% by weight of the compound of formula (I) on the weight of the polymer will be found satisfactory and between about 0.2% and 2% will be preferred.

The compound of formula (I) may be used in the polymer alone or in combination with other additives, such as fillers, antioxidants, flame retardants, heat stabilizers, anti-slipping and anti-static agents, supplemental light stabilizers, pigments, dyes, lubricants, etc.

The compounds of formula (I) can be prepared by reacting an aminoalcohol of formula (II) with a cyclohexanone of formula (III) to produce a compound of formula (I) as illustrated by the following reaction wherein $R_1$, $R_2$, $R_3$ and $R_4$ are as previously defined and X is —H, or alkyl of 1 to 8 carbon atoms.

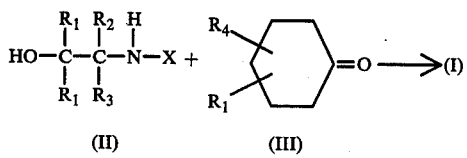

The preparations of many compounds of formula (I) can be found in the literature. For example, Pierce et al., J.A.C.S. 73, 2595 (1951) and Hancock et al., J.A.C.S. 66, 1751 (1944) describe the preparation of 3,3-dimethylol-1-oxa-4-azaspiro[4.5]decane and 3-methyl-3-methylol-1-oxa-4-azaspiro[4.5]decane, respectively.

The compounds of formula (I) wherein X is —O· can be obtained by oxidizing those compounds wherein X is —H with an oxidizing agent such as hydrogen peroxide or perbenzoic acid. The compounds of formula (I) wherein X is —OH can be obtained by reducing those compounds wherein X is —O· with hydrogen.

Illustrative of the compounds represented by formula (I) are the following:
3-methyl-3-methylol-1-oxa-4-azaspiro[4.5]decane,
3,3-dimethylol-1-oxa-4-azaspiro[4.5]decane,
3,3-dimethylol-2-methyl-1-oxa-4-azaspiro[4.5]decane,
2,3,3-trimethyl-1-oxa-4-azaspiro[4.5]decane,
3,3-dimethyl-8-nonyl-1-oxa-4-azaspiro[4.5]decane,
3,3-dimethyl-8-dodecyl-1-oxa-4-azaspiro[4.5]decane,
3,3,6-trimethyl-1-oxa-4-azaspiro[4.5]decane,
3,3-dimethyl-2-octyl-1-oxa-4-azaspiro[4.5]decane,
3,3,4-trimethyl-1-oxa-4-azaspiro[4.5]decane,
3,3-dimethyl-4-octyl-1-oxa-4-azaspiro[4.5]decane,
3,3-dimethylol-4-methyl-1-oxa-4-azaspiro[4.5]decane,
3,3-di(2-hydroxyethyl)-1-oxa-4-azaspiro[4.5]decane,
3,3,6,8-tetramethyl-1-oxa-4-azaspiro[4.5]decane,
3,3-dimethyl-4-hydroxy-1-oxa-4-azaspiro[4.5]decane,
3,3-dimethyl-4-oxide-1-oxa-4-azaspiro[4.5]decane,
3,3-dimethylol-4-hydroxy-1-oxa-4-azaspiro[4.5]decane, 3,3-dimethyl-4-hydroxy-8-nonyl-1-oxa-4-azaspiro[4.5]-decane and the like.

Illustrative of suitable antioxidants useful with the formula I compounds are those of the hindered-phenol type, such as 2,6-di-t-butyl-p-cresol; 4,4'-bis(2,6-di-t-butylphenol); 4,4'-bis(2,6-di-iso-propylphenol); 2,4,6-tri-t-butylphenol; 2,2'-thiobis(4-methyl-6t-butylphenol); octadecyl 2(3',5'-di-t-butyl-4'-hydroxyphenyl)-propionate; etc.; esters of thiodipropionic acid, such as dilauryl thiodipropionate and distearyl thiodipropionate, etc.; hydrocarbyl phosphites, such as triphenyl phosphite, trinonyl phosphite, diphenyl-decyl phosphite, etc.; and combinations thereof.

Illustrative of the supplemental light stabilizers which may be used are those of the benzotriazole class, such as 2-(2'-hydroxy-5'-octylphenyl)benzotriazole; 2-[2'-hydroxy-3',5'-di-t-butylphenyl]-5-chlorobenzotriazole; those of the hydroxybenzophenone type, such as 2-hydroxy-4-methoxybenzophenone; 2-hydroxy-4-octyloxybenzophenone; 2,2'-dihydroxy-4,4'-dimethoxybenzophenone; hindered phenol esters, such as 2',4'-di-t-butylphenyl 3,5-di-t-butyl-4-hydroxybenzoate; metal complexes, such as nickel complexes of 2,2'-thiobis(4-6-octylphenol); nickel butylamine complex of 2,2'-thiobis(4-t-octylphenol); nickel complexes of bis(4-t-octylphenyl)sulfone; nickel dibutyl dithiocarbamate; nickel salts of 4-hydroxy-3,5-di-t-butylbenzyl phosphonic acid monoalkyl esters where alkyl is methyl, ethyl, propyl, butyl, etc.; nickel complex of 2-hydroxy-4-methylphenyl undecyl ketone oxime; etc. Further illustrative examples of suitable antioxidants and of suitable supplemental light stabilizers can be found in columns 3 and 4 of U.S. Pat. Nos. 3,488,290 and 3,496,134 and the other patents mentioned therein.

The following examples, in which parts and percentages are by weight unless otherwise stated, are presented to further illustrate the present invention.

EXAMPLE 1

Preparation of
3,3-Dimethylol-1-Oxa-4-Azaspiro[4.5]Decane

Tris-(hydroxymethyl)-aminomethane (24.23 grams; 0.2 mole) and cyclohexanone (19.63 grams; 0.2 mole) were refluxed overnight in 150 mls of toluene, using a water separator to remove approximately 3.6 mls of water. The toluene was then removed by distillation and the residue was recrystallized from acetone to obtain 32 grams (79.5% of theoretical; m.p. 117°–119° C.) of the desired compound.

EXAMPLE 2

Preparation of
3-Methyl-3-Methylol-1-Oxa-4-Azaspiro[4.5]Decane

The procedure of Example 1 was employed utilizing 2-amino-2-methyl-1,3-propanediol (42.05 grams; 0.4 mole) and cyclohexanone (39.26 grams; 0.4 mole) in 250 mls of toluene. After removing the toluene, the residue was distilled to obtain 37.7 grams (50.8% of theoretical; b.p. 120° C. at 2.0 mm.) of the desired compound.

EXAMPLE 3

Preparation of
3,3-Dimethyl-8-Nonyl-1-Oxa-4-Azaspiro[4.5]Decane

The procedure of Example 1 was followed utilizing 1,1-dimethylethanolamine (2.7 grams; 0.03 mole) and 4-n-nonylcyclohexanone (6.73 grams; 0.03 mole) in 100 mls of toluene. After removing the toluene, the residue was distilled to obtain 4.3 grams (48.5% of theoretical; b.p. 113°–115° C. at 0.01 mm.) of the desired product.

EXAMPLE 4

Preparation of 2-Nonyl-2,4,4-Trimethyl-Oxazolidine

The procedure of Example 1 was followed utilizing 1,1-dimethylethanolamine (22.3 grams; 0.25 mole) and methyl n-nonylketone (42.6 grams; 0.25 mole) in 250 mls of toluene. After removing the toluene, the residue was distilled to obtain 26.7 grams (44% of theoretical; b.p. 92°–94° C. at 0.3 mm.) of the desired product. This product was prepared for comparison with the compounds of Examples 1–3.

EXAMPLES 5–8

Evaluation of Light Stabilization Properties

The compound under test was incorporated at 0.5% by weight into unstabilized polypropylene (Pro-Fax$^R$6401; Hercules, Inc.) with 0.2% by weight of a processing antioxidant, 2,4,6-tri-t-butylphenol, by dry-blending and milling at 350°–370° F. on a standard plastic mill for 5 minutes, and compression molding the compositions into films (4–5 mils thick) at 400° F. The film was then exposed to ultraviolet light in a Xenon Arc Weather-Ometer (Atlas Electric Devices Co.) until the carbonyl content of the film was increased by 0.10%, as determined by infrared spectrophotometric measurement. A control film identically prepared without the compound under test was also exposed to the light until the carbonyl content increased by 0.10%.

EXAMPLE 5

The product of Example 1 was incorporated in polypropylene as described above and evaluated for light stability. The film required 1200 hours exposure to increase the carbonyl content by 0.10%. A control film required only 500 hours to increase the carbonyl content by 0.10%.

EXAMPLE 6

The product of Example 2 was incorporated in polypropylene, as described above, and the film was evaluated for light stability. The film required 800 hours exposure to increase the carbonyl content by 0.10%. A control film required only 500 hours to increase the carbonyl content by 0.10%.

Similar results are obtained by substituting a copolymer of propylene and ethylene (Pro-Fax$^R$7723; Hercules, Inc.) for the polypropylene.

EXAMPLE 7

The product of Example 3 was incorporated in polypropylene as described above and the film was evaluated for light stability. The film required 1300 hours exposure to increase the carbonyl content by 0.10%. A control film required only 400 hours to increase the carbonyl content by 0.10%.

Similar results are obtained by substituting 2,3,-3-trimethyl-1-oxa-4-azaspiro[4.5]decane; 2-isopropyl-3,3-dimethylol-1-oxa-4-azaspiro[4.5]decane; 3,3-dimethylol-4-hydroxy-1-oxa-4-azaspiro[4.5]decane; 3,3-dimethyl-4-oxide-1-oxa-4-azaspiro[4.5]decane; or 3,3-dimethylol-4-methyl-1-oxa-4-azaspiro[4.5]decane for the product of Example 3.

EXAMPLE 8

The product of Example 4, a comparison compound, was incorporated in polypropylene as described above and the film was evaluated for light stability. The film required only 400 hours exposure to increase the carbonyl content by 0.10%. A control film required 300 hours to increase the carbonyl content by 0.10%.

What is claimed is:

1. A polymer composition containing an effective amount of a compound of the formula (I)

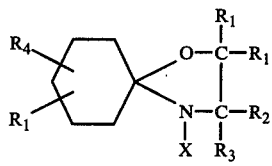

wherein each $R_1$ is selected from hydrogen and alkyl having 1 to 8 carbon atoms; $R_2$ and $R_3$ are each selected from alkyl or hydroxyalkyl having 1 to 8 carbon atoms; $R_4$ is hydrogen or alkyl having 1 to 18 carbon atoms and X is —H, —OH, —O·, or alkyl having 1 to 8 carbon atoms, to stabilize said polymer against degradation by ultraviolet radiation.

2. A composition as defined in claim 1 wherein said polymer is a polyolefin.

3. A composition as defined in claim 2 wherein said polyolefin is polypropylene.

4. A composition as defined in claim 1 wherein said effective amount is about 0.1% to about 5% by weight of said compound on the weight of the polymer.

5. A composition as defined in claim 1 wherein said compound is 3,3-dimethylol-1-oxa-4-azaspiro[4.5]decane.

6. A composition as defined in claim 1 wherein said compound is 3-methyl-3-methylol-1-oxa-4-azaspiro[4.5]decane.

7. A composition as defined in claim 1 wherein said compound is 3,3-dimethyl-8-nonyl-1-oxa-4-azaspiro[4.5]decane.

8. A method for stabilizing a polymer against degradation by ultraviolet radiation comprising incorporating in said polymer a stabilizing amount of a compound of formula (I) as defined in claim 1.

* * * * *